(12) United States Patent
Birkhold et al.

(10) Patent No.: US 12,053,320 B2
(45) Date of Patent: Aug. 6, 2024

(54) COMPUTER-IMPLEMENTED METHOD, COMPUTER PROGRAM, SYSTEMS AND X-RAY FACILITY FOR CORRECTION OF X-RAY IMAGE DATA WITH REGARD TO NOISE EFFECTS

(71) Applicant: Siemens Healthcare GmbH, Erlangen (DE)

(72) Inventors: Annette Birkhold, Nuremberg (DE); Philipp Roser, Erlangen (DE)

(73) Assignee: Siemens Healthineers AG, Forchheim (DE)

(*) Notice: Subject to any disclaimer, the term of this patent is extended or adjusted under 35 U.S.C. 154(b) by 313 days.

(21) Appl. No.: 17/236,330

(22) Filed: Apr. 21, 2021

(65) Prior Publication Data
US 2021/0330274 A1  Oct. 28, 2021

(30) Foreign Application Priority Data

Apr. 22, 2020 (DE) .................... 10 2020 205 121.6

(51) Int. Cl.
*G06N 3/08* (2023.01)
*A61B 6/00* (2006.01)

(52) U.S. Cl.
CPC ............. *A61B 6/5282* (2013.01); *G06N 3/08* (2013.01)

(58) Field of Classification Search
CPC ... A61B 6/5282; A61B 6/5205; A61B 6/4441; G06N 3/08; G06N 3/045
See application file for complete search history.

(56) References Cited

U.S. PATENT DOCUMENTS

| 6,058,322 A | * | 5/2000 | Nishikawa | ............ | G06T 7/0012 |
| | | | | | 382/128 |
| 2010/0220906 A1 | * | 9/2010 | Abramoff | ........... | G06F 18/2415 |
| | | | | | 382/165 |
| 2019/0066268 A1 | * | 2/2019 | Song | ....................... | G06T 5/002 |

FOREIGN PATENT DOCUMENTS

CN  101526465 A  *  9/2009
DE  102019215242 A1   4/2021

OTHER PUBLICATIONS

Translation of CN-101526465-A (Year: 2009).*
(Continued)

*Primary Examiner* — David P Porta
*Assistant Examiner* — Mamadou Faye
(74) *Attorney, Agent, or Firm* — Lempia Summerfield Katz LLC (57) ABSTRACT

A computer-implemented method and system for providing a trained artificial intelligence determination algorithm for correcting x-ray image data with regard to noise effects, for example for scattered radiation correction of the x-ray image data. The determination algorithm, from input data comprising a recorded image dataset, determines a noise effect dataset describing the noise effects to be used for correction of the x-ray image dataset. A statistical physics model parameterized by model parameters is used to describe the noise effects. The model parameters are able to be determined at least in part using the determination algorithm including receiving of training datasets that include x-ray image sub datasets with assigned, known noise effect sub datasets and/or with at least one assigned, noise-free reference image sub dataset, training the determination algorithm using the training datasets, and providing the trained determination algorithm.

20 Claims, 6 Drawing Sheets

(56) References Cited

OTHER PUBLICATIONS

German Office Action for German Application No. 10 2020 205 121.6 dated Dec. 8, 2020.

Maier, Joscha, et al. "Real-time scatter estimation for medical CT using the deep scatter estimation: Method and robustness analysis with respect to different anatomies, dose levels, tube voltages, and data truncation." Medical physics 46.1 (2019): 238-249.

Maslowski, Alexander, et al. "Acuros CTS: A fast, linear Boltzmann transport equation solver for computed tomography scatter—Part I: Core algorithms and validation." Medical physics 45.5 (2018): 1899-1913.

* cited by examiner

COMPUTER-IMPLEMENTED METHOD, COMPUTER PROGRAM, SYSTEMS AND X-RAY FACILITY FOR CORRECTION OF X-RAY IMAGE DATA WITH REGARD TO NOISE EFFECTS

CROSS REFERENCE TO RELATED APPLICATIONS

This application claims the benefit of DE 102020201070.6 filed on Jan. 29, 2020, which is hereby incorporated by reference in its entirety.

FIELD

Embodiments relate to a computer-implemented method for providing a trained artificial intelligence determination algorithm for carrying out a process of correcting x-ray image data with regard to noise effects occurring during the recording of the x-ray image data, for example for scattered radiation correction of the x-ray image data, wherein the determination algorithm determines from input data including a recorded image dataset a noise effect dataset describing the noise effects to be used for correction of the x-ray image dataset. Embodiments also provide a method for correction of x-ray image data with regard to such noise effects, for example for scattered radiation correction of the x-ray image data wherein, using at least one x-ray image dataset as input data, a noise effect dataset describing the noise effects is determined and is used for correction of the x-ray image dataset, for example by subtraction.

BACKGROUND

X-ray imaging is an established modality, for example in medical diagnostics and/or intervention monitoring. During x-ray imaging an x-ray emitter is used to x-ray an examination object to be recorded, for example a patient, whereupon the x-ray radiation, after passing through the examination object, is measured again by an x-ray detector, in modern x-ray facilities usually a flat-panel detector. Depending on the passage through heavily attenuating materials on the x-ray path, a greater or lesser attenuation of the x-ray radiation is caused by the examination object, so that thus x-ray image data from usual two-dimensional x-ray images (projection images/fluoroscopy images) is understood as intensity values.

In such cases it is ever more frequently common to record two-dimensional x-ray images of an examination region of the examination object using different recording geometries, for example using different projection directions, in order to obtain by reconstruction three-dimensional information about the examination region, for example a three-dimensional x-ray image (volume dataset). This technique is known as computed tomography, in which specific computed tomography facilities are employed, that usually have a gantry in which a recording arrangement or at least an x-ray emitter may be rotated about a patient.

Other x-ray facilities for three-dimensional imaging are also used. For example, x-ray facilities with a C-arm be used, on which an x-ray emitter and an x-ray detector are arranged as a recording arrangement at opposite ends of the C-arm, in order to obtain projection images of a patient using different projection directions. This is referred to as "dynamic CT" for example and may be usefully employed within the framework of minimally-invasive interventions or in similar environments.

As with any other measurement technique, with x-ray imaging too, undesired but unavoidable effects may occur, that may have an influence on the result of the imaging, thus on an x-ray image dataset obtained, that may also contain a number of two-dimensional projection images. A well-known effect of this type is scattered radiation captured by the x-ray detector, caused by various effects. Scattered radiation, in interventional fluoroscopy for example, for example with a C-arm x-ray facility, represents a major contribution to the degradation of the image quality. In two-dimensional fluoroscopy or radiography lower contrast or uneven radiation exposure caused by scattered radiation may greatly reduce the diagnostic value of the two-dimensional x-ray image. In three-dimensional x-ray imaging, i.e., in computed tomography, streaking and cupping artifacts may occur with the framework of the reconstruction.

In order to avoid scattered radiation effects, for example scattered radiation artifacts, in x-ray image data, scattered radiation grids (anti-scatter grids) may be installed in front of the x-ray detector, in order to physically block scattered radiation mostly entering laterally. However, this leads not just to the blocking of scattered radiation but also of primary radiation, so that a markedly higher radiation dose is needed for the patient, to which the medical personnel are also exposed. Such scattered radiation grids or anti-scatter grids may further also cause new types of artifacts to occur, since for example the grids may also be recorded themselves in the x-ray images.

Thus, in the prior art, various computer-implemented, software-based methods have already been proposed for rectifying noise effects from scattered radiation in x-ray image data entirely or at least for reducing them. In such methods different approaches are known in the prior art, that all have certain disadvantages, however. A first, simple approach uses filters, may thus also be referred to as a kernel-based approach. Although such approaches are extremely fast in the provision of corrections, they are however less accurate, since they are formulated as object-independent and may only map linear effects.

A second approach is the use of Monte-Carlo simulations of the imaging process, in order, in this manner, by mapping the physics of imaging as completely as possible, to determine noise effect datasets, here scattered radiation datasets, that quantitatively describe scattered radiation at the different pixels and thus may be employed easily for correction of a respective x-ray image dataset, for example by pixel-by-pixel subtraction. Such Monte-Carlo simulation approaches, although they are accurate, may only be implemented with difficulty however, since the approaches require a wide-ranging prior knowledge in relation to the geometry of the examination object, for example of the patient, and need dedicated hardware acceleration to enable the approaches to be implemented at all. Even then however there are likely to be long processing times.

In an article by Joscha Maier et al., entitled "Real-time scatter estimation for medical CT using the deep scatter estimation: Method and robustness analysis with respect to different anatomies, dose levels, tube voltages, and data truncation", Med. Phys. 46 (1), January 2019, Pages 238-249, it was proposed in this regard, as a substitute for the Monte-Carlo approaches expensive in terms of computing effort, to make a scattered radiation correction in real time possible by employing as the artificial intelligence determination algorithm a Deep Convolutional Network, that predicts Monte-Carlo simulated scattered radiation estimations based on the recorded x-ray image data. As a result, the "deep scatter estimation" (DSE) generalizes well in respect of different tube voltages, noise levels and anatomical regions, provided these are sufficiently represented in the training data. Thus, almost the same accuracy as in Monte-Carlo simulations is obtained, but with far faster computability.

In concrete terms a U network, thus a sequence of encoders and decoders, is used there in order to determine from an incoming x-ray image dataset an associated noise effect dataset, here a scattered radiation dataset. In this case, because of the complexity of the process to be mapped, namely the Monte-Carlo simulation, an extremely large number of free parameters is trained in the Deep Convolutional Network, that involves a high outlay and throws up questions in respect of robustness and applicability to specific clinical problems. Moreover, there is an extremely strong dependence on the quality of the training data.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a computational correction of noise effects that is improved compared to the method, for example for scattered radiation correction, for example in respect of robustness.

Embodiments provide a computer implemented training method. The computer-implemented method provides a trained artificial intelligence determination algorithm for carrying out a correction process of x-ray image data with regard to noise effects occurring during imaging, for example for scattered radiation correction of the x-ray image data. The determination algorithm determines from input data including a recorded x-ray image dataset a noise effect dataset describing the noise effects to be used for correction of the x-ray image dataset. A statistical physics model parameterized by model parameters is used for description of the noise effects. The model parameters are established at least in part by using the determination algorithm. The method includes the following steps, receiving of training datasets, that include x-ray image sub datasets with assigned known noise effect sub datasets and/or with at least one assigned, error-free reference image dataset, training of the determination algorithm using the training datasets, and providing the trained determination algorithm.

The correction approaches described here or the provision of correction described here relate for example to scattered radiation correction during x-ray imaging, for example when using an x-ray facility with a C-arm and/or in interventional x-ray imaging, but it has been shown that the method of operation may also be applied for further noise effects of low spatial frequency that arise during the recording process per se. In this case noise effects of low spatial frequency are, for example, to be understood as the noise effects varying over far greater length scales than the structures of the examination object to be resolved by the x-ray imaging, for example anatomical structures of a patient. For scattered radiation effects for example this type of low spatial frequency has been shown with usually a number of spatially separated maxima. Therefore, scattered radiation correction is a key field of application of the trained artificial intelligence determination algorithm, where for example a scattered radiation dataset may then be established as the noise effect dataset, that for example describes quantitatively pixel-by-pixel the strength of the scattered radiation effects and thus may be employed for correction by pixel-by-pixel subtraction from the x-ray image dataset.

A trained artificial intelligence determination algorithm, that may also be referred to as a trained determination function, is provided or applied. A trained function or a trained artificial intelligence algorithm maps cognitive functions that connect humans with other human intelligences. For example, a trained function, through training based on training data, is capable of adapting itself to new circumstances and of detecting and extrapolating patterns.

A trained function may be adapted by training (machine learning). For example, supervised learning, semi-supervised learning, unsupervised learning, reinforcement learning and/or active learning may be employed. What is more, so-called representation learning (also known as feature learning) may be employed. The parameters of the trained functions may be adapted iteratively through various training or machine learning steps.

A trained function or a trained artificial intelligence algorithm may include a neural network, a support vector machine, a decision tree and/or a Bayesian network. The trained function may further be based on k-means clustering, Q learning, genetic algorithms and/or association rules. For example, a neural network may be a deep neural network, a Convolutional Neural Network (CNN) or a deep convolutional neural network. A neural network may further be an adversarial network, a deep adversarial network and/or a Generative Adversarial Network (GAN).

The artificial intelligence determination algorithm that is employed provides an implicitly or explicitly used estimation of the noise effects in the examination region covered by the x-ray image dataset. In this case however, by contrast with the prior art, either by the configuration of the artificial intelligence determination algorithm itself but also forced by the training data used, an abstract map, for example of an entire Monte-Carlo simulation, is no longer delivered, but a physics model that is physically meaningful and/or actually mapping the physics underlying the noise effects, making do with far fewer free parameters is employed. Embodiments provide a method of operation based on machine learning, that in the form of the physics model, uses a mathematical description of the noise effects, for example of the scattered radiation, preferably in the projection image domain, i.e., for two-dimensional x-ray images.

Scattered radiation distributions, or low-frequency noise effect distributions, may be parameterized in two-dimensional x-ray images (2D radiographs), by approximation theory and/or stochastic theory procedures being employed, in concrete terms parametric physics models, that not only offer the advantage of a greatly reduced number of free parameters in the determination algorithm, but also, as will be explained in greater detail, offer the opportunity to take account of further physical-technical effects and of accommodating them as well in the model mapping given by the determination algorithm.

In this way embodiments provide physically meaningful noise effect estimations, for example scattered radiation distributions, to be provided by a learning-based method. Weaknesses of previous approaches of the prior art, for example too great a number of free parameters, long inference times, dubious applicability and the like are overcome, while at the same time results of equal or better quality are obtained. Since there are fewer free parameters present, embodiments for example also allow fewer training data to be employed than comparable artificial intelligence approaches, so that training and maintenance may be realized with lower outlay. Since high-quality correction information may be provided in real time, embodiments may also render the use of anti-scatter grids superfluous, so that the costs and the effort for example for superior x-ray facilities may be further reduced.

If the trained artificial intelligence determination algorithm is used, the low-dimensional set of model parameters may be inferred directly from the x-ray image data of the x-ray image dataset (inference). In such cases extremely short interference times, for example run times of the determination algorithm for a specific x-ray image dataset in the region of 5 ms, may be obtained. This makes it possible for example, that will be discussed below in further detail, to integrate a correction carried out by the trained determination algorithm into the image chain and/or the reconstruction pipeline.

The physics model may include a univariate or bivariate or multivariate polynomial model and/or a univariate or bivariate or multivariate spline model and/or a probability density model combining a number of a probability density functions. The physics models, that may also be referred to as approximation models, are each defined by a low-dimensional set of model parameters. Multivariate probability density function mixture models combining a number of probability density functions may for example include Gaussian distributions (defined by average values and standard deviations), student's t-distributions, Poisson distributions and the like. In such cases, in the cases of noise effects to be mapped, for example with scattered radiation effects, there are usually a number of spatially distributed maxima present, so that mixed models are needed.

Spline-based physics models, for example B splines, that are correspondingly defined by control coefficients, are advantageous. The scattered radiation distribution in a two-dimensional 320×240-x-ray image may be approximated by 12×9 B spline coefficients with an error of less than 1%.

Spatially low-frequency noise effects, for example scattered radiation distributions, have been described by the physics model. One embodiment provides, in the definition of the physics model and/or the selection of the model parameters and/or in the training of the determination algorithm, for at least one boundary condition suppressing structures of a spatial frequency exceeding a threshold value to be used in a noise effect dataset established by the model parameters determined by the determination algorithm. In other words, the physics model may be forced to be spatially low-frequency, so that the manipulation or changing of spatially high-frequency image details, for example anatomical details during imaging of a patient as examination object are largely avoided if possible. In this case the physics model may already be set up so that it only describes spatially low-frequency structures, for example by model parameters that would reproduce high-frequency structures being excluded from the outset. A corresponding restriction of the artificial intelligence determination algorithm in this way also brings with it the advantage that the number of model parameters and thus of the free, trainable parameters, may be drastically reduced, so that a more robust application and the possibility of training with fewer items of training data arises. The positioning of this restriction or its implementation may depend for example, as will be explained in greater detail below, on whether the physics model is superimposed externally on the artificial intelligence determination algorithm or is internal, thus for example as one or more layers of a corresponding neural network. In such cases however it may be preferred to force the restriction to lower spatial frequencies through an appropriate choice of the physics model and its model parameters.

Different approaches exist that make it possible to force the trained artificial intelligence determination algorithm implicitly or explicitly to map the physics model, wherein a mandatory condition superimposed on the determination algorithm internally, for example a fixed, explicit formulation of the physics model in one or more layers not to be trained, and also where necessary the inclusion of further portions of the determination algorithm that cannot be changed by the learning process, allow further advantageous options for bringing about an accurate correction better reflecting the actual noise effects.

In an embodiment, the training model parameters for the training datasets may be determined by fitting the physics model to the noise effect sub dataset of the training dataset, after which the training model parameters are used as training output data for training. In this case an explicit fit of the physics model to the noise effect sub dataset contained in the training datasets in each case is undertaken for the training data, in order to train the artificial intelligence determination algorithm for output of corresponding model parameters as output data during the use of at least the x-ray image dataset as input data. In this embodiment the artificial intelligence determination algorithm thus uses input data, that at least include the x-ray image dataset, and delivers output data, that contain the associated model parameters, so that the correspondingly assigned noise effect dataset may be easily determined by using the physics model. Such fitting of the physics model, for example of a bivariate B spline model, corresponds to a loss-free down-sampling by a factor of around 20 to 30. In this embodiment a simple convolutional neural network, for example an encoder, is sufficient. The model parameters, when used later by the determination algorithm, may then be concluded (inferred) with reference to a current x-ray image dataset, according to which the model parameters will be evaluated on a predefined image grid, that corresponds to the image grid of the x-ray image dataset. The noise effect dataset obtained in this way may then for example be subtracted pixel-by-pixel from the x-ray image dataset in order to bring about the correction.

In an embodiment, the application of the physics model in the artificial intelligence determination algorithm may be integrated as an additional component that is not to be trained, for example as at least one layer. The determination algorithm is trained directly on the basis of the noise effect sub datasets of the training datasets as training output data. The model parameters are still only implicitly determined within the determination algorithm, but that this determination is forced by the additional component implementing the physics model and not able to be changed by the training, so that the model parameters will certainly also continue to be available as intermediate results. The determination algorithm uses at least the x-ray image dataset as input data and then outputs the noise effect dataset as output data.

In this embodiment, the physics model may be mapped in a linear manner which is utilized to integrate it into the determination algorithm, for example the neural network. For example, B splines may be integrated as linear mapping into the determination algorithm. In this way a kind of end-to-end training is allowed, meaning that an additional fit process is no longer necessary, but the x-ray image sub dataset and the noise effect sub dataset of the training dataset may be employed directly for training. This makes possible the use of more sophisticated regularization approaches, so that more robust results may be obtained.

An embodiment may provide for a non-negativity of the corrected x-ray image dataset to be used as a boundary condition in the training process. A mandatory condition may be used, that insures the non-negativity of a corrected x-ray image dataset.

An embodiment may provide, when the ultimate imaging goal is a 3D x-ray image, for the application of the physics model and a reconstruction of a 3D x-ray image from two-dimensional x-ray images of the x-ray image dataset to be integrated into the artificial intelligence determination algorithm as supplementary components that are not to be trained, for example each as at least one layer. The determination algorithm is trained directly on the basis of the reference image sub datasets of the training datasets as training output data. The training datasets may however continue to contain the noise effect sub datasets, so that ultimately it is known how the noise effects look in the projection domain, but also how the image completely cleaned of the noise effects looks in the reconstructed 3D space. The former may also be derived from the latter.

An embodiment may accept the reconstruction operators, for example the filtered back projection, as a supplementary component into the artificial intelligence determination algorithm. This is possible since such reconstruction operators are (sub) differentiable and thus may be integrated easily into a neural network as layers not to be trained. Thus, for example in applications that in any event aim for a three-dimensional reconstruction and the obtaining of a 3D x-ray image that is as free of artifacts as possible, a determination algorithm is trained and provided in this manner, that directly delivers the desired end result, namely the corrected, artifact-reduced three-dimensional volume dataset, for example without or at least with greatly reduced scatter artifacts. The reference image sub dataset then contains the noise-free reference 3D x-ray image for the x-ray image sub dataset. Here too an end-to-end training is thus possible in respect of 3D x-ray images, that also allows additional regularization and the use of loss metrics both in the projection domain and also in the reconstruction domain.

For example, with x-ray image data of a patient as examination object, a boundary condition promoting a predefined homogeneity in the image data, for example a limit value to the total variation (TV) is used. This is because human bodies are known usually to have essentially homogeneous regions, for example specific organs and/or tissue types.

However the acceptance of supplementary components into the determination algorithm, here for example of the physics model itself or reconstruction, if in the corresponding layers/additional components no free, i.e. trainable parameters are contained, brings with it advantages, since not only, as explained, improved regularization and loss metrics may be employed in order to force desired results or to take account of prior knowledge, but also the back propagation of errors may be exploited in an improved manner.

In general terms the training datasets may be determined through computation, for example simulation, and/or through measurement. In such cases, the training datasets may be established at least in part by a Monte-Carlo simulation of an imaging process. When training datasets are to be provided there is also a greater amount of time available, so that the Monte-Carlo simulations reproducing the physics extremely accurately may be carried out without problems, for example also in respect of the fact that, because of a much reduced number of model parameters, that actually form the free parameters of the determination algorithm, compared with previous artificial intelligence approaches, a smaller number of training data is sufficient or far better results may be obtained with the same number of training data.

However other approaches have already been proposed, in order as well as to arrive at x-ray image datasets, also to arrive at the noise effect datasets reflecting the basic truth, for example in scattered radiation correction. For example, a measurement may be taken with a grid in front of the x-ray emitter, that is then also visible in the x-ray image, so that corresponding conclusions may be drawn by computation. However, these types of measurement approaches, such as for example the so-called, primary modulation just mentioned, are mostly extremely complex by comparison with Monte-Carlo simulations. But also with regard to such computational or simulational approaches there are already variations and methods of operation known in the prior art, that may be employed to obtain training data, wherein the reader is referred just purely by way of example to the approach of Alexander Maslowski et al., "Acuros CTS: A fast, linear Boltzmann transport equation solver for computed tomography scatter—Part I: Core algorithms and validation", Med. Phys. 45 (5), May 2018, Pages 1899-1913.

The determination algorithm may be specifically determined for specific recording parameters and/or may use specific recording parameters as further input data as well as the x-ray image dataset and/or may already map variations in specific recording parameters itself. In the article cited at the beginning by Joscha Maier et al. it has been shown that a generalized approach in respect of different recording parameters, for example different tube voltages at the x-ray emitter, different noise levels or different anatomical regions, may already be present, that may also be implemented, so that a single determination algorithm for different concrete applications/imaging processes, for example different imaging protocols, may be employed. However even when variations or deviations may no longer be robustly mapped, there is always the option of training and having available a further determination algorithm and/or of undertaking a further parameterization of the determination algorithm, for example, in that at least one recording parameter is also used as an input data item.

As has already been explained, the artificial intelligence determination algorithm may involve a neural network. A convolutional neural network (CNN), for example an encoder, may be used. In a CNN, for example an encoder, the input dataset, for example the x-ray image dataset, is mapped to a far lower amount of data, for example the model parameters. In embodiments described above the encoder may then be followed by the supplementary component for example, in order to determine from the model parameters, the noise effect dataset or the corrected, reconstructed 3D x-ray image.

Embodiments provide a correction method, e.g., a method for correction of x-ray image data with regard to noise effects, for example for scattered radiation correction of the x-ray image data. Using at least one x-ray image dataset as input data, a noise effect dataset describing the noise effects is established and is used for correction of the x-ray image dataset, for example through pixel-by-pixel subtraction. A physics model statistically parameterized by model parameters may be used to describe the noise effects. The model parameters are established at least in part by using an artificial intelligence determination algorithm, that uses the x-ray image dataset as input data and the noise effect dataset is established by applying the model parameters determined to the physics model.

The general remarks with regard to the provision method still apply accordingly for the correction method, so that within the framework of the correction method there may especially advantageously be provision for the determination algorithm to be provided by a provision method.

The correction method too thus also for example uses the approach of forcing a description in accordance with a physics model in an artificial intelligence determination algorithm by training or its concrete formulation, in order in this way with a low-dimensional model parameter set, to be able to determine a description of the noise effects, for example the scattered radiation distribution. For example, the possibilities for training already mentioned may be employed. For the correction method, the physics model may include a univariate or bivariate or multivariate polynomial model and/or a univariate or bivariate or multivariate spline model and/or a probability density model combining a number of a probability density functions. A spline model, for example a bivariate B spline model, may be used. In the correction method, the determination algorithm further includes a convolutional neural network, for example an encoder, for determining the model parameters.

Embodiments also provide a computer program that carries out the steps of the provision method and/or of the correction method when it is executed on a computing facility, for example a provision system and/or a correction system. The computer program may be stored on an electronically-readable data medium, that thus contains control information that includes at least one computer program and is configured in such a way that, when the data medium is used in a computing facility, a provision method and/or correction method is carried out. The electronically-readable data medium for example involves a non-transient data medium, for example a CD-ROM.

Embodiments provide a provision system for providing a trained artificial intelligence determination algorithm for carrying out a correction process of x-ray image data with regard to noise effects, for example for scattered radiation correction of the x-ray image data. The determination algorithm, from input data including a recorded x-ray image dataset, determines a noise effect dataset describing the noise effects to be used for correction of the x-ray image dataset. The provision system includes a first interface for receiving training datasets, that include x-ray image sub datasets with assigned known noise effect sub datasets and/or with at least one assigned, noise-free reference image sub dataset, a computation unit for training the determination algorithm by using the training datasets, wherein a statistical physics model parameterized by model parameters is used for describing the noise effects, wherein the model parameters are able to be determined at least in part using the determination algorithm, and a second interface for providing the trained determination algorithm.

All remarks relating to the provision method may be transferred accordingly to the provision system. The provision system may for example have at least one computing facility, for example with at least one processor and/or a storage. The first interface, the computation unit and/or the second interface may be implemented accordingly by the processing facility, for example by hardware and/or software.

A correction system for correction of x-ray image data relating to noise effects, for example for scattered radiation correction of the x-ray image data, includes a first interface for receiving an x-ray image dataset, a correction unit and a second interface for output of a correction result. Using the x-ray image dataset as input data, the correction unit is configured for establishing a noise effect dataset describing the noise effects and further for correction of the x-ray dataset, for example through pixel-by-pixel subtraction, using the noise effect dataset. In accordance with the invention there is now provision, for such a correction system, for a statistical physics model parameterized by model parameters to be used for description of the noise effects, in that an artificial intelligence determination algorithm is stored in the correction unit, that uses as input data the x-ray image dataset and determines the associated model parameters. The correction unit is further configured to determine the noise dataset by applying the established model parameters to the physics model.

The correction system may also have at least one processing facility, for example with at least one processor and/or a storage. The processing facility provides the first interface, the correction unit and the second interface to be realized. All remarks relating to the correction method also still apply accordingly to the correction system.

The correction system is configured to be used directly in an x-ray facility, so that the correction is done there as part of the image chain, for example the correction system is thus realized as part of the imaging system.

Embodiments provide an x-ray facility including a control device for processing received x-ray datasets, for example an imaging system, that is configured for carrying out a correction method and/or include a correction system.

A user directly obtains corrected x-ray images at the x-ray facility, for example as the at least one x-ray image of the x-ray image dataset itself and/or as an x-ray image derived therefrom, for example a reconstructed 3D image. Noise effects have been reduced or removed entirely. For example, a scattered radiation correction has then already been undertaken within the usual image chain. For example, an anti-scatter grid may the also be dispensed with.

For the x-ray facility the remarks relating to the correction method and the correction system still apply, so that the advantages given there or what has already been stated about the provision method still apply.

BRIEF DESCRIPTION OF THE FIGURES

Further advantages and details of the present invention emerge from the exemplary embodiments described below as well as with reference to the drawings. In the figures.

DETAILED DESCRIPTION

Figure 1:
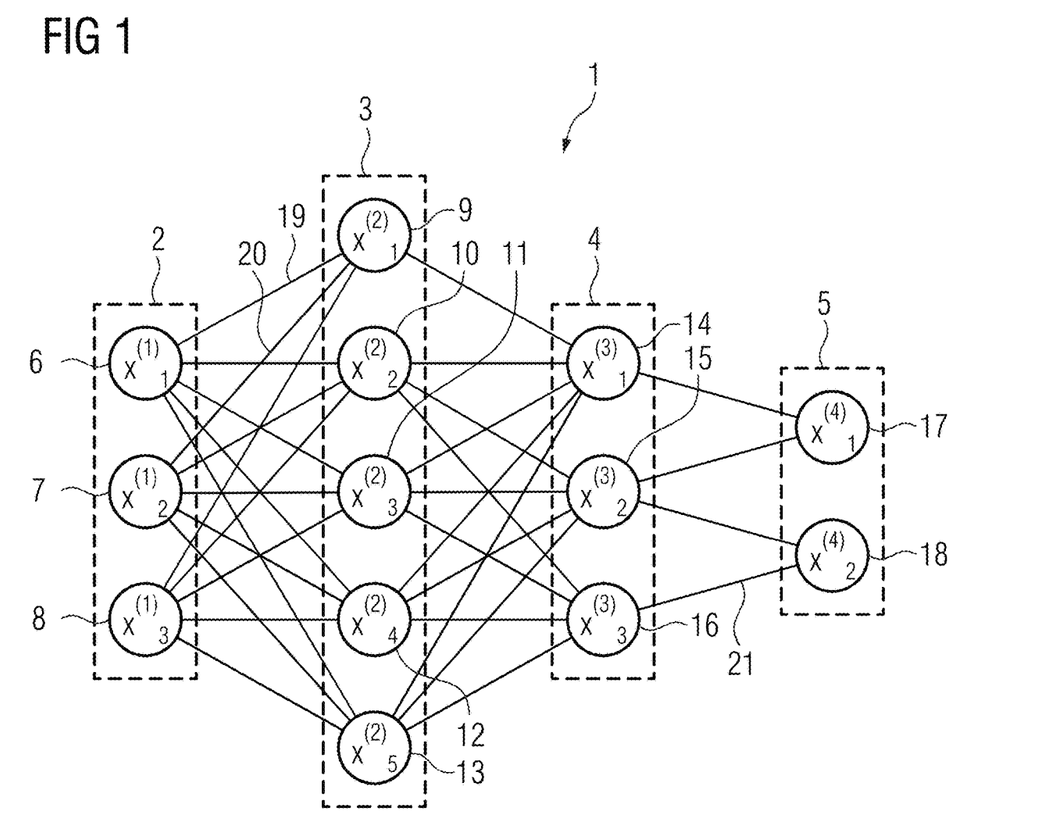
FIG. 1 depicts an embodiment of an artificial neural network.

FIG. 1 depicts an embodiment of an artificial neural network 1. Other terms for the artificial neural network 1 are neural network, artificial neural net or neural net.

The artificial neural network 1 includes nodes 6 to 18 and edges 19 to 2. Each edge 19 to 21 is a directed connection from a first node 6 to 18 to a second node 6 to 18. The first node 6 to 18 and the second node 6 to 18 are different nodes 6 to 18, but it is also conceivable however for the first node 6 to 18 and the second node 6 to 18 to be identical. For example, in FIG. 1 the edge 19 is a directed connection from the node 6 to the node 9 and the edge 21 is a directed connection from the node 16 to the node 18. An edge 19 to 21 from a first node 6 to 18 to a second node 6 to 18 is referred to as an ingoing edge for the second node 6 to 18 and as an outgoing edge for the first node 6 to 18.

In this embodiment the nodes 6 to 18 of the artificial neural network 1 may be arranged in layers 2 to 5. The layers may have an intrinsic order, that is introduced by the edges 19 to 21 between the nodes 6 to 18. For example, edges 19 to 21 may only be provided between neighboring layers of node 6 to 18. In the embodiment shown there exists an input layer 110, that includes the nodes 6, 7, 8, each without an incoming edge. The output layer 5 includes only the nodes 17, 18, each without an outgoing edge, wherein further hidden layers 3 and 4 lie between the input layer 2 and the output layer 5. In one case any number of hidden layers 3, 4 may be chosen. The number of nodes 6, 7, 8 of the input layer 2 may correspond to the number of input values in the neural network 1, and the number of nodes 17, 18 in the output layer 5 may correspond to the number of output values in the neural network 1.

For example, a (real) number may be assigned to the nodes 6 to 18 of the neural network 1. In such cases $x^{(n)}_i$, refers to the value of the ith node 6 to 18 of the nth layer 2 to 5. The values of the nodes 6, 7, 8 of the input layer 2 are equivalent to the input values of the neural network 1, while the values of the nodes 17, 18 of the output layer 5 are equivalent to the output values of the neural network 1. each edge 19, 20, 21 may be assigned a weight in the form of a real number. For example, the weight is a real number in the range $[-1, 1]$ or in the range $[0, 1,]$. In this case $w^{(m,n)}_{i,j}$ refers to the weight of the edge between the ith node 6 to 18 of the mth layer 2 to 5 and the jth node 6 to 18 of the nth layer 2 to 5. The abbreviation $w^{(n)}_{i,j}$ is further defined for the weight $w^{(n,n+1)}_{i,j}$.

In order to compute output values of the neural network 1, the input values are propagated through the neural network 1. For example, the values of the nodes 6 to 18 of the (n+1)th layer 2 to 5 may be calculated based on the values of the nodes 6 to 18 of the nth layers 2 to 5 by $$x_j^{(n+1)} = f(\Sigma_i x_i^{(n)} \cdot w_{i,j}^{(n)}).$$

In this case f is a transfer function, that may also be referred to as an activation function. Known transfer functions are step functions, sigmoid functions (for example the logistical function, the generalized logistical function, the tangens hyperbolicus, the arctangent, the error function, the smoothstep function) or rectifier functions. The transfer function may be used for normalization purposes.

For example, the values are propagated layer-by-layer through the neural network 1. Values of the input layer 2 are given by the input data of the neural network 1. Values of the first hidden layer 3 may be computed based of the values of the input layer 2 of the neural network 1, values of the second hidden layer 4 may be computed based of the values in the first hidden layer 3 etc.

In order to provide the values $w_{i,j}^{(n)}$ for the edges 19 to 21 to be defined, the neural network 1 must be trained using training data. For example, training data includes training input data and training output data, that will be referred to below as $t_i$. For a training step the neural network 1 is applied to the training input data, in order to determine computed output data. For example, the training output data and the computed output data includes a number of values, wherein the number is defined as the number of nodes 17, 18 of the output layer 5.

For example, a comparison between the computed output data and the training output data is used in order to adapt the weights within the neural network 1 recursively (back propagation algorithm). For example, the weights may be changed in accordance with $$w'^{(n)}_{i,j} = w^{(n)}_{i,j} - \gamma \cdot \delta_j^{(n)} \cdot x_i^{(n)}$$

wherein $\gamma$ is a learning rate and the numbers $\delta_j^{(n)}$ may be computed recursively as $$\delta_j^{(n)} = \Sigma_k \delta_k^{(n+1)} \cdot w_{j,k}^{(n+1)}) \cdot f'(\Sigma_i x_i^{(n)} \cdot w_{i,j}^{(n)})$$

based on $\delta_j^{(n+1)}$, when the (n+1)th layer is not the output layer 5, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)th layer is the output layer 5, wherein f' is the first derivation of the activation function and $y_j^{(n+1)}$ is the comparison training value for the jth node 17, 18 of the output layer 5.

An example for a Convolutional Neural Network (CNN) is also given below in respect of FIG. 2. The expression "layer" is provided in a slightly different way to the way in which it is used for classical neural networks. For a classical neural network, the expression "layer" only refers to the set of nodes that form a layer, thus to a specific generation of nodes. For a convolutional neural network, the expression "layer" is often used as an object that actively changes data, for example as a set of nodes of the same generation and either the set of incoming or outgoing edges.

Figure 2:
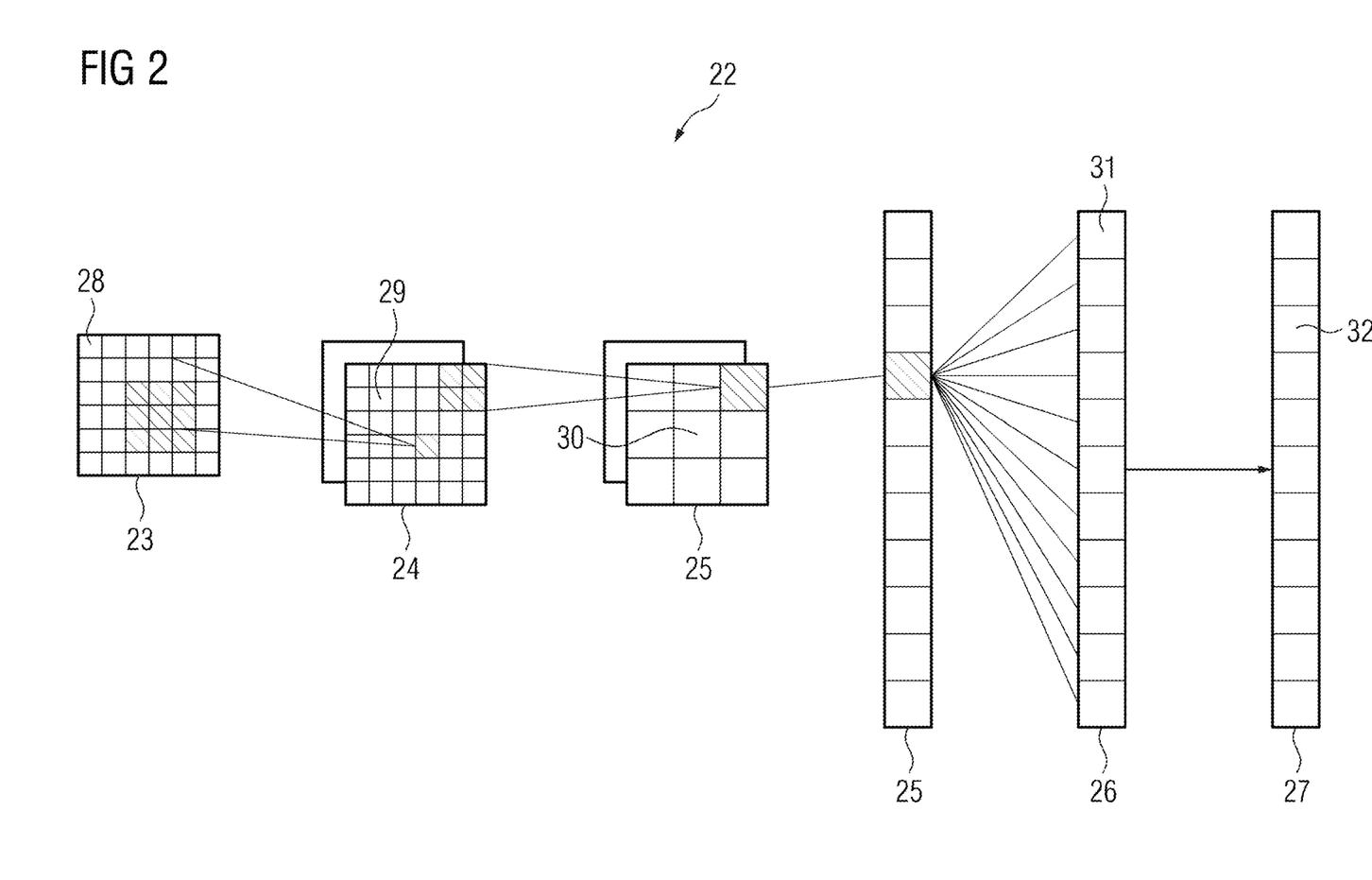
FIG. 2 depicts an embodiment of a convolutional neural network.

FIG. 2 depicts an embodiment of a convolutional neural network 22. In the embodiment shown the convolutional neural network 22 includes an input layer 23, a convolutional layer 24, a pooling layer 25, a fully connected layer 26 and an output layer 27. In alternate embodiments the convolutional neural network 22 may contain a number of convolutional layers 24, a number of pooling layers 25 and a number of fully connected layers 26, exactly like other types of layers. Any given sequence may be selected for the sequence of the layers, wherein usually fully connected layers 26 form the last layers before the output layer 27.

For example, within a convolutional neural network 22, the nodes 28 to 32 of one of the layers 23 to 27 may be understood as arranged as a d-dimensional matrix or as a d-dimensional image. In the two-dimensional case for example, the value of a node 28 to 32 with the indices i, j in the nth layer 23 to 27 may be referred to as $x^{(n)}[i,j]$. The arrangement of the nodes 28 to 31 of a layer 23 to 27 has no effect on the calculations within the convolutional neural network 22 as such, since these effects are exclusively given by the structure and the weights of the edges.

A convolutional layer 24 is for example characterized in that the structure and the weights of the ingoing edges forms a convolution operation based on a specific number of kernels. For example, the structure and the weights of the ingoing edges is selected so that the values $x_k^{(n)}$ of the node 29 of the convolutional layer 24 is established as a convolution $x_k^{(n)} = K_k * x^{(n-1)}$ based on the values $x^{(n-1)}$ of the node 28 of the preceding layer 23, wherein the convolution * may be defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i', j-j'].$$

In this the kth kernel $K_k$ is a d-dimensional matrix, in this embodiment a two-dimensional matrix, that is small by comparison with the number of nodes 28 to 32, for example a 3×3 matrix or a 5×5 matrix. For example, this implies that the weights of the ingoing edges are not independent, but are selected so that they create the above convolution equation. In the example for a kernel that forms a 3×3 matrix, only nine independent weights exist (wherein each entry of the kernel matrix corresponds to one independent weight), regardless of the number of nodes 28 to 32 in the corresponding layers 23 to 27. For example, for a convolutional layer 24 the number of nodes 29 in the convolutional layer 24 is equivalent to the number of nodes 28 in the preceding layer 23 multiplied by the number of convolution kernels.

When the nodes 28 of the preceding layer 23 are arranged as a d-dimensional matrix, the use of the plurality of kernels may be understood as the addition of a further dimension, that is also referred to as a depth dimension, so that the nodes 29 of the convolutional layer 24 are arranged as a (d+1)-dimensional matrix. When the nodes 28 of the preceding layer 23 are already arranged as a (d+1)-dimensional matrix with a depth dimension, the use of a plurality of convolution kernels may be understood as an expansion along the depth dimension, so that the nodes 29 of the convolutional layer 24 are similarly arranged as a (d+1)-dimensional matrix. The size of the (d+1)-dimensional matrix in the depth dimension is greater by the factor formed by the number of the kernels than in the preceding layer 23.

The advantage of the use of convolutional layers 24 is that the spatial local correlation of the input data may be utilized by a local connection pattern being created between nodes of neighboring layers, for example by the fact that each node only includes connections to a small area of the nodes of the preceding layer.

In the embodiment shown the input layer 23 includes thirty-six nodes 28, that are arranged as a two-dimensional 6×6 matrix. The convolutional layer 24 includes seventy-two nodes 29, that are arranged as two two-dimensional 6×6-matrices. Each of the two matrices is the result of a convolution of the values of the input layer 23 with a convolution kernel. In the same way the nodes 29 of the convolutional layer 24 may be understood as arranged as a three-dimensional 6×6×2 matrix. The last-mentioned dimension is the depth dimension.

A pooling layer 25 is characterized in that the structure and the weights of the ingoing edges as well as the activation function of their nodes 30 define a pooling operation based on a non-linear pooling function f. In the two-dimensional case for example the values $x^{(n)}$ of the nodes 30 of the pooling layer 25 may be calculated based on the values $x^{(n+1)}$ of the nodes 29 of the preceding layer 24 as $$x^{(n)}[i,j]=f(x^{(n-1)}[id_1,jd_2], \ldots, x^{(n-1)}[id_1+d_1-1,jd_2+d_2-1]).$$

The use of a pooling layer 25 provides the number of nodes 29, 30 to be reduced, in that a number $d_1 \times d_2$ of neighboring nodes 29 in the preceding layer 24 is replaced by a single node 30, that is calculated as a function of the values of the number of neighboring nodes 29. For example, the pooling function f may be a maximum function, an averaging or the L2 norm. For example, for a pooling layer 25, the weights of the ingoing edges may be fixed and not be able to be modified by training.

The advantage of the use of a pooling layer 25 is that the number of the nodes 29, 30 and the number of the parameters is reduced. This leads to a reduction in the necessary amount of calculation within the convolutional neural network 22 and thus to a control of the overfitting.

In the embodiment shown the pooling layer 25 involves a max pooling layer, in which four neighboring nodes are replace with just one single node, the value of which is formed by the maximum of the values of the four neighboring nodes. The max pooling is applied to each d-dimensional matrix of the preceding layer; in this embodiment the max pooling is applied to each of the two two-dimensional matrices, so that the number of nodes is reduced from seventy-two to eighteen.

A fully connected layer 26 is characterized in that a plurality, for example all, edges are present between the node 30 of the preceding layer 25 and the nodes 31 of the fully connected layer 26. The weight of each of the edges may be individually configured. In this embodiment the nodes 30 of the preceding layer 25 and the fully connected layer 26 are shown both as two-dimensional matrices and also as non-contiguous nodes (shown as a row of nodes, wherein the number of nodes has been reduced so that they may be shown more easily). In this embodiment the number of nodes 31 in the fully connected layer 26 is equal to the number of nodes 30 in the preceding layer 25. In alternate embodiments the number of nodes 30, 31 may be different.

In an embodiment the values of the nodes 32 of the output layer 27 are specified by the softmax function being applied to the values of the nodes 31 of the preceding layer 26. By applying the softmax function the sum of the values of all nodes 32 of the output layer 27 is one and all values of all nodes 32 of the output layer are real numbers between 0 and 1. When the convolutional neural network 22 is used for classification of input data, the values of the output layer 27 may be interpreted for example as the likelihood of the input data falling into one of the different classes.

A convolutional neural network 22 may include a ReLU layer, wherein ReLU is an acronym that stands for "rectified linear units". For example, the number of nodes and the structure of the nodes within a ReLU layer is equivalent to the number of nodes and the structures of the nodes of the preceding layer. The value of each node in the ReLU layer may be calculated for example by applying a rectifier function to the value of the corresponding node of the preceding layer. Examples of rectifier functions are $f(x) = \max(0,x)$, the hyperbolic tangent or the sigmoid function.

Convolutional neural networks 22 may be trained for example based on the back propagation algorithm. To avoid an overfitting, regularization methods may be employed, for example dropout of individual nodes 28 to 32, stochastic pooling, use of artificial data, weight decay based on the L1 norm or the L2 norm or maximum norm restrictions.

Figure 3:
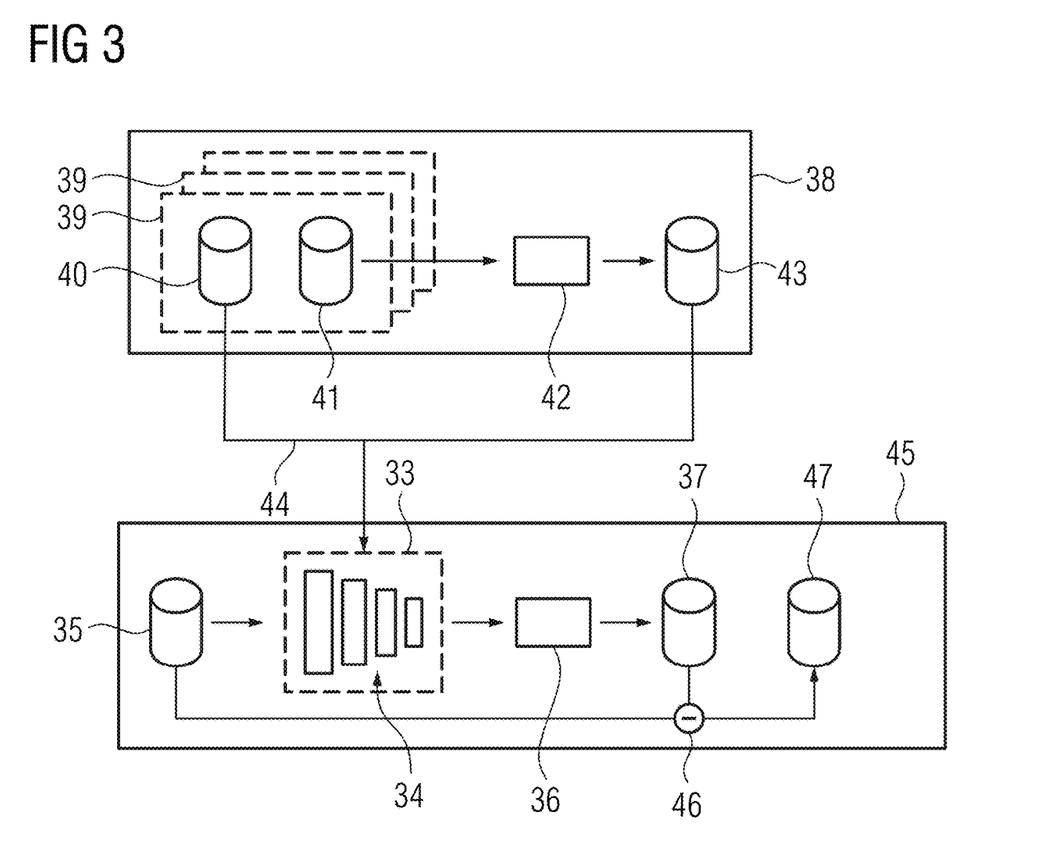
FIG. 3 depicts a system sketch of an embodiment.

FIG. 3 depicts a system sketch of an embodiment of the present invention. In FIG. 3 both a provision method (training method) and also a correction method are explained, that applies correspondingly for the embodiments described in respect of FIGS. 4 and 5.

In FIG. 3 an artificial intelligence determination algorithm 33 is used, that in FIG. 3 includes a convolutional neural network 34. The determination algorithm 33 may be used to derive model parameters of a physics model from input data, that includes an x-ray image dataset 35 recorded with an x-ray facility, in the present example a bivariate B spline model. The physics model, when the model parameters determined by the determination algorithm 33, that form the output data, are specified, is capable, as the application of the physics model in step 36 indicates, of determining a noise effect dataset 37, that in the present example describes the scattered radiation distribution during the recording of the x-ray image dataset 35. A plurality of training datasets 39 is provided in a training phase 38, for example by Monte-Carlo simulations, as is known. Each training dataset 39 in this case in the present example contains an x-ray image sub dataset 40 (corresponds to the x-ray image dataset 35) and a noise effect sub dataset 41 (corresponds to the noise effect dataset 37).

In a preparatory step 42 the scattered radiation distribution 41 determined through simulation for the x-ray image sub dataset 40 is fitted to the physics model, so that training model parameters 43 are produced, that may be used as training output data for the training input data (x-ray image sub datasets 40).

The physics model is defined by the choice of the model parameters so that it maps the noise effects in the low spatial frequencies usual for it, thus structures of a spatial frequency exceeding a threshold value, thus for example anatomical structures, to be mapped, of patient as examination object, are not or not appreciably adversely affected by the correction measures.

As indicated by the arrow 44, the training input data (x-ray image sub datasets 40) and training output data (training model parameters 43) assembled in this way are then used to train the determination algorithm 33, for example the convolutional neural network 34. The convolutional neural network 34 represents an encoder, as a large number of input data items (x-ray image dataset 35) is converted into a far smaller number of output data items (model parameters).

In an embodiment, the scattered radiation distribution is mapped by the bivariate B-spline model by a small number of model parameters, that results in a smaller number of free parameters in determination algorithm 33, that may thus be trained robustly with little training data and extremely quickly, for example in fewer than 10 ms, for example fewer than 5 ms, provides the corresponding model parameters and thus noise effect datasets 37 to be inferred (inference) from x-ray image datasets 35.

If the trained determination algorithm 33 is provided, it may initially be used in a correction phase 45, as already explained at the start, to determine the noise effect dataset 37 for an x-ray image dataset 35 currently being recorded, and through pixel-by-pixel subtraction, may be used in a step 46 to provide a corrected x-ray image dataset 47.

Figure 4:
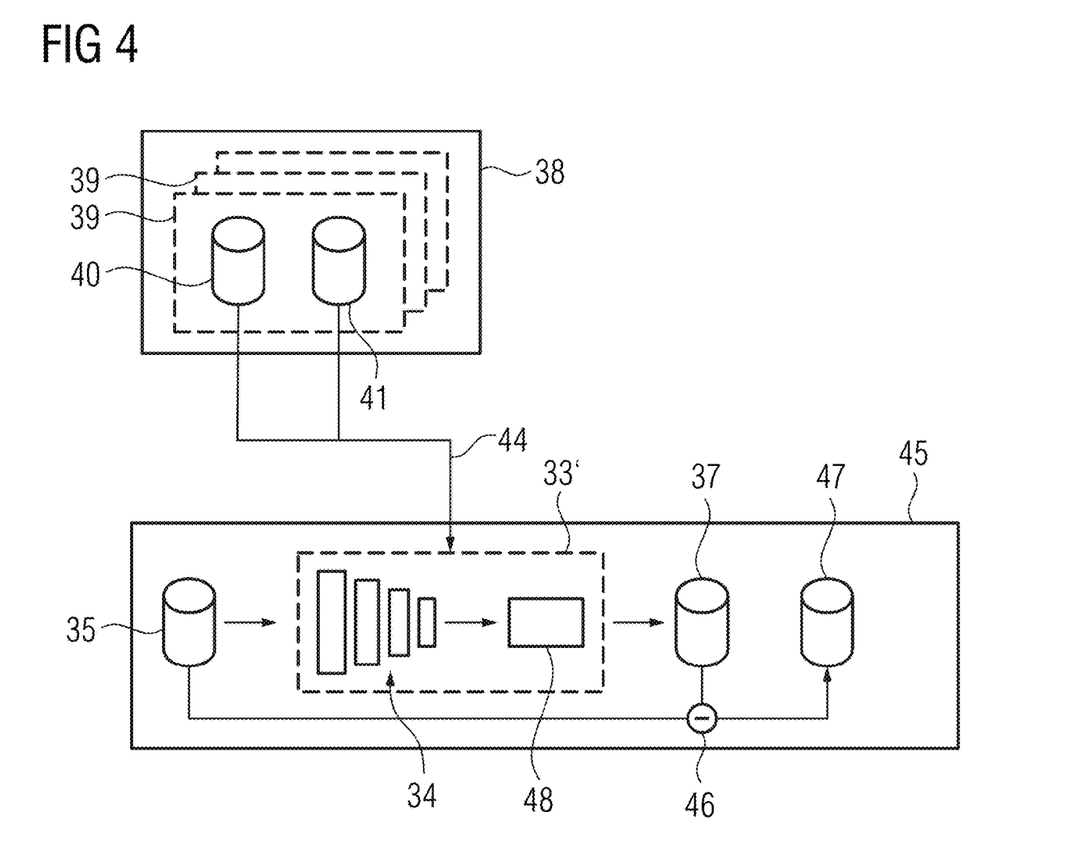
FIG. 4 depicts a system sketch of an embodiment.
Figure 5:
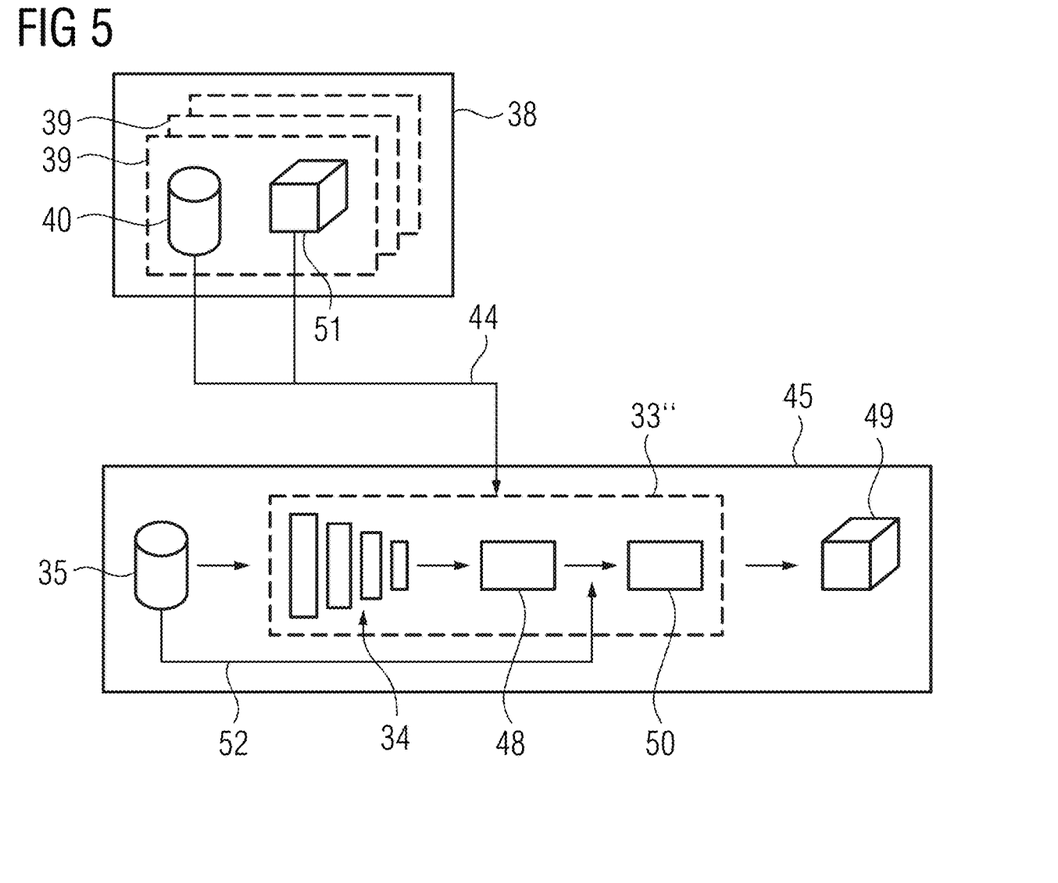
FIG. 5 depicts a system sketch of an embodiment.

The method of operation described here may be applied to a plurality of different x-ray image datasets 35. For example, an application to purely two-dimensional examination processes, for example two-dimensional fluoroscopy or two-dimensional radiography, may be used. The x-ray image dataset 35 may then for example contain one or more two-dimensional x-ray images of a single recording geometry. This embodiment as well as the following embodiments of FIGS. 4 and 5 are however also applicable to three-dimensional examination processes, for example computed tomography measurements and/or computed tomography-type measurements, in which 3D x-ray images are to be reconstructed from a plurality of two-dimensional x-ray images recorded from different projection directions (projection images). The x-ray image dataset 35 may contain all these two-dimensional x-ray images.

FIG. 4 depicts an embodiment modified by comparison with that shown in FIG. 3. The same reference characters are used for objects with the same function. It may be seen that the embodiment differs from the other embodiments in the definition of the artificial intelligence determination algorithm 33'. In this figure, in addition to convolutional neural network 34, this has a supplementary component 48 containing at least one layer, that contains the application of the physics model, in FIG. 3 step 36 or the fitting step 42. This supplementary component 48 is fixed and forces so to speak the physically meaningful model structure in the determination algorithm 33', that makes it possible to use the x-ray image sub datasets 40 and the noise effect sub datasets 41 as training input data and training output data. Accordingly, the trained determination algorithm 33' also delivers the noise effect dataset 37 directly as output data in this case.

In the embodiment in accordance with FIG. 4 the fact that the application of the physics model is also included as supplementary component 48 in the determination algorithm 33' is used, in that a further peripheral condition for forcing physically meaningful results is employed, namely the requirement for non-negativity of the corrected x-ray image dataset 47.

FIG. 5 depicts an embodiment of the correction method with the provision method, as may be applied when, through x-ray examination of the x-ray image dataset 35, 3D-x-ray images 49 (volume datasets) are to be reconstructed, the x-ray image dataset 35 thus contains a plurality of two-dimensional x-ray images recorded from different projection directions. In the present case a determination algorithm 33" is used, that once again contains the convolutional neural network 34 and the supplementary component 48, that corresponds to the application of the physics model, but in this case however also a mapping of the reconstruction operators, for example of the filtered back projection, as at least one further layer of the overall neural network, in this example as a further supplementary component 50. This means that as output data the determination algorithm 33" now delivers the already corrected, reconstructed 3D x-ray image 49. However, the supplementary component 50 is also predetermined as fixed, thus contains no free parameters that will be trained.

Accordingly, the training datasets 39, as well as the x-ray image sub datasets 40, now contain reference image sub datasets 51 assigned to these, that correspond to the corrected, noise-free 3D x-ray image for the x-ray image sub dataset 40. By this training input data and training output data an end-to-end training once again takes place. In addition to the non-negativity condition already mentioned for corrected x-ray image data, a further boundary condition is used, that requires a predetermined homogeneity in the image data. For example, a limit value for the total variation may be employed here. In this way account is taken of the fact that patients usually have extensive regions of substantial homogeneity in the three-dimensional.

The input data in the determination algorithm 33', i.e., the x-ray image datasets 35, as indicated by the arrow 52, is used internally a further time, for example to determine the corrected x-ray image dataset 47, that then serves as the starting point for the reconstruction by the supplementary component 50. The determination algorithm 33" also internally retains the use of the basic method of operation of initially determining the model parameters through the convolutional neural network 34, i.e., the encoder, of determining and correcting the noise effect datasets 37 by the supplementary component 48, once again by pixel-by-pixel subtraction, after which the three-dimensional reconstruction is then undertaken in the supplementary component 50, for example as filtered back projection.

Figure 6:
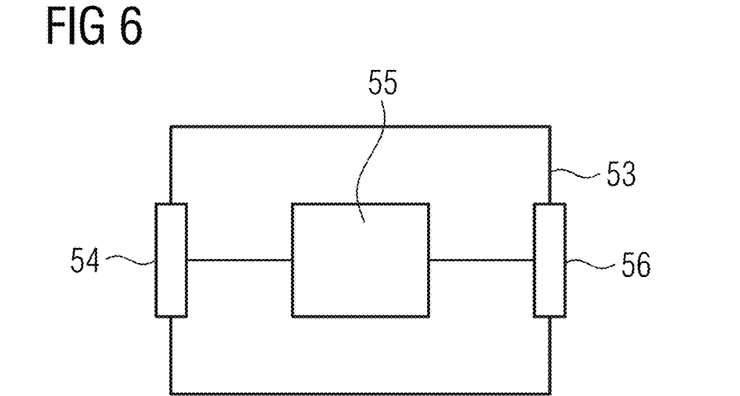
FIG. 6 depicts functional components of a provision system according to an embodiment.

FIG. 6 depicts the functional structure of a provision system 53 configured to provide the training phases 38 of one of the embodiments in FIG. 3, 4 or 5. The provision system 53 includes a first interface 54 in order to receive the training datasets 39. The training is done in a computation unit 55, as described, wherein where necessary the computation unit 55 may be embodied as in the case of FIG. 3 for carrying out the fit and for determining the training model parameters 43 in step 42. In each case the training step indicated by the arrow 44 is carried out by the computation unit 55. The trained determination algorithm 33, 33', 33" is then provided to a second interface 56.

Figure 7:
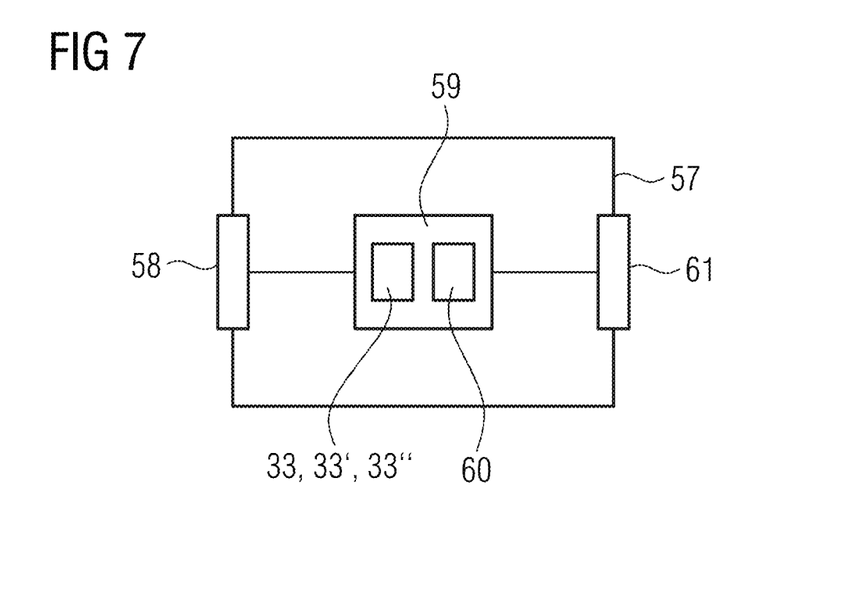
FIG. 7 depicts functional components of a correction system according to an embodiment.

FIG. 7 correspondingly depicts the structure of a correction system for carrying out the correction phases 45 of one of the embodiments in accordance with FIG. 3, 4 or 5. The correction system 57 includes a first interface 58 for receiving the x-ray image dataset 35 to be corrected. Stored in a correction unit 59 is at least the artificial intelligence trained determination algorithm 33, 33', 33". In the embodiments of FIG. 3 and FIG. 4 a subtraction unit 60 may be included. The correction result may be output via a second interface 61.

Figure 8:
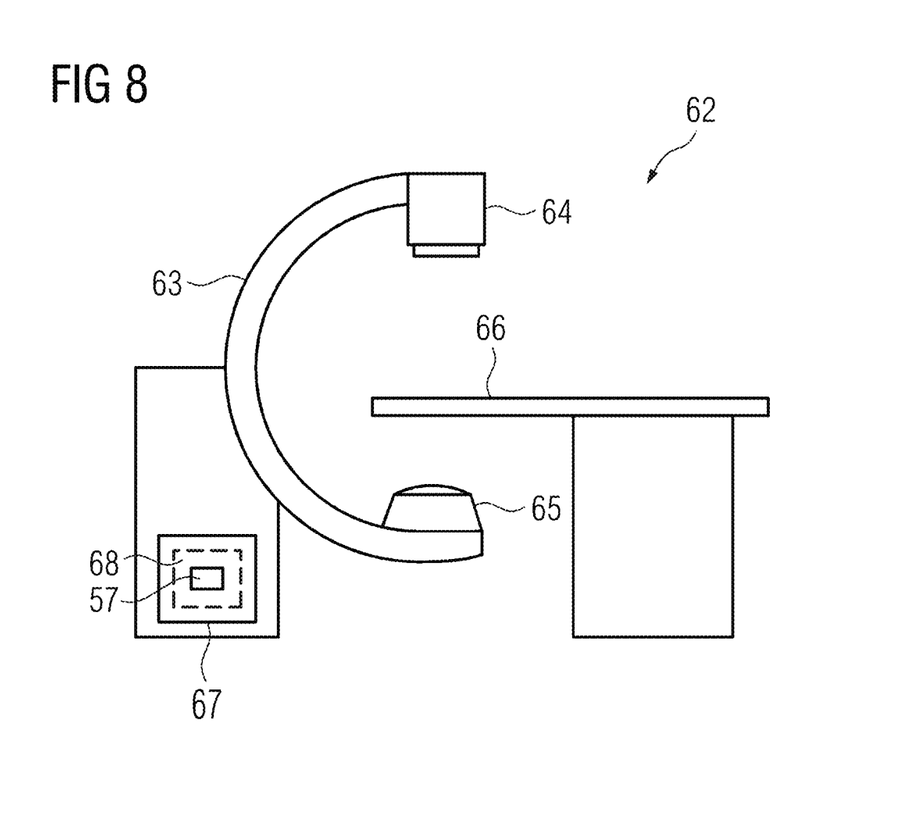
FIG. 8 depicts an x-ray facility according to an embodiment.

FIG. 8 depicts a sketch of an x-ray facility 62. This for example involves an x-ray facility with a C-arm 63, on which an x-ray emitter 64 and an x-ray detector 65 are arranged opposite one another as a recording arrangement. A patient to be accommodated may be supported on a patient couch 66. Because of the adjustability or for example rotatability of the C-arm 63 it is possible, for example during an intervention into a patient positioned on the patient couch 66, to record two-dimensional x-ray images (projection images) of an examination region of the patient from different projection angles, in order to reconstruct a 3D x-ray image from the images, as described. Fluoroscopic and other two-dimensional applications are also possible.

The operation of the x-ray facility 62 is controlled by a control device 67, that in the present example includes an imaging system 68 realizing the imaging chain, through which x-ray image data, that has been recorded with the recording arrangement 64, 65, is processed in such a way that the desired imaging result is produced and may be displayed on a display device (not shown) for example of the x-ray facility 62. Various processing steps of the x-ray image data are carried out within the imaging chain of the imaging system 68, that are possible in real time. The processing steps also include the correction described here using the determination algorithm 33, 33' or 33", that maps the scattered radiation distribution via a physically motivated physics model, so that the imaging system 68 for example also contains an inventive correction system 57.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing a trained determination algorithm for carrying out a correction process of x-ray image data with regard to noise effects, wherein the trained determination algorithm, when input data comprising a recorded x-ray image dataset, determines a noise effect dataset describing noise effects to be used for correction of the x-ray image data, wherein a physics model statistically parameterized by model parameters is applied for describing the noise effects, wherein the model parameters are determined at least in part by using the trained determination algorithm, the method comprising:
    receiving one or more training datasets that each comprise x-ray image sub datasets with assigned known noise effect sub datasets, with at least one assigned, error-free reference image dataset, or with assigned known noise effect sub dataset and at least one assigned, error-free reference image dataset;
    training of a determination algorithm using the training datasets; and
    providing the trained determination algorithm.

2. The method of claim 1, wherein the correction process comprises scattered radiation correction of the x-ray image data.

3. The method of claim 1, wherein the physics model comprises at least one of a univariate or bivariate or multivariate polynomial model, a univariate or bivariate or multivariate spline model, or a probability density function model combining a number of a probability density functions.

4. The method of claim 1, wherein for at least one of a definition of the physics model, a choice of the model parameters, or the training of the determination algorithm at least one boundary condition suppressing structures of a spatial frequency exceeding a threshold value is used in a noise effect dataset determined by the model parameters determined by the trained determination algorithm.

5. The method of claim 1, wherein training model parameters for the training datasets are established by fitting the physics model to the noise effect sub datasets of the training dataset after which the training model parameters are used as training output data for training.

6. The method of claim 1, wherein a user of the physics model in the determination algorithm is integrated as a supplementary component not to be trained, for example as at least one layer, wherein the determination algorithm is trained directly as training output data based on the noise effect sub datasets of the training datasets.

7. The method of claim 1, wherein the application of the physics model and a reconstruction of a 3D x-ray image from two-dimensional x-ray images of the x-ray image data are integrated into the trained determination algorithm as supplementary components that are not trained, for example in each case as at least one layer, wherein the determination algorithm is trained directly as training output data based on the reference image sub datasets of the training datasets.

8. The method of claim 1, wherein the one or more training datasets are determined at least in part by a Monte-Carlo simulation of an imaging process.

9. The method of claim 1, wherein the determination algorithm comprises a convolutional neural network configured to determine the model parameters.

10. A method for correction of x-ray image data with regard to noise effects, the method comprising:
    inputting at least one x-ray image dataset;
    determining a noise effect dataset that describes the noise effects using a physics model statistically parameterized by model parameters; and
    correcting the x-ray image dataset with the noise effect dataset;
    wherein the model parameters are determined by a trained determination algorithm that inputs the x-ray image dataset and determines the noise effect dataset by applying the model parameters determined by applying the model parameters to the physics model.

11. The method of claim 10, wherein the trained determination algorithm is trained using one or more training datasets that each comprise x-ray image sub datasets with assigned known noise effect sub datasets, with at least one assigned, error-free reference image dataset, or with assigned known noise effect sub dataset and at least one assigned, error-free reference image dataset.

12. The method of claim 10, wherein the correction comprises scattered radiation correction of the x-ray image data.

13. A provision system for providing a trained determination algorithm for carrying out a correction process of x-ray image data with regard to noise effects wherein a trained determination algorithm determines, from input data comprising a recorded x-ray image dataset, a noise effect dataset describing the noise effects that is used for correction of the x-ray image data, the provision system comprising:
- a first interface implemented by a processing facility including at least one processor and storage, the first interface configured to receive one or more training datasets that each comprise x-ray image submasters with assigned known noise effect sub datasets, at least one assigned, noise-free reference image sub dataset, or assigned known noise effect sub datasets and at least one assigned, noise-free reference image sub dataset;
- a computation unit implemented by the processing facility, the computation unit configured to train the determination algorithm using the one or more training datasets, wherein a physics model statistically parameterized by model parameters is used to describe the noise effects, wherein the model parameters are determined at least partly using the determination algorithm; and
- a second interface implemented by the processing facility, the second interface configured to provide the trained determination algorithm.

14. The provision system of claim 13, wherein the correction process comprises scattered radiation correction of the x-ray image data.

15. The provision system of claim 13, wherein the physics model comprises at least one of a univariate or bivariate or multivariate polynomial model, a univariate or bivariate or multivariate spline model, or a probability density function model combining a number of a probability density functions.

16. The provision system of claim 13, wherein for at least one of a definition of the physics model, a choice of the model parameters, or the training of the determination algorithm, at least one boundary condition suppressing structures of a spatial frequency exceeding a threshold value is used in a noise effect dataset determined by the model parameters determined by the trained determination algorithm.

17. The provision system of claim 13, wherein training model parameters for the training datasets are established by fitting the physics model to the noise effect sub dataset of the training dataset after which the training model parameters are used as training output data for training.

18. The provision system of claim 13, wherein a user of the physics model in the determination algorithm is integrated as a supplementary component not to be trained, for example as at least one layer, wherein the determination algorithm is trained directly as training output data based on the noise effect sub datasets of the training datasets.

19. A correction system for correction of x-ray image data with regard to noise effects, the correction system comprising:
- a first interface implemented by a processing facility including at least one processor and storage, the first interface configured to receive an x-ray image dataset;
- a correction unit implemented by the processing facility, the correction unit configured to determine, using the x-ray image dataset as input data, a noise effect dataset describing the noise effects, the correction unit further configured to correct the x-ray image dataset using the noise effect dataset, wherein a physics model statistically parameterized by model parameters is used for describing the noise effects, wherein a trained determination algorithm is stored in the correction unit, the trained determination algorithm configured to use the x-ray image dataset as input data in order to output associated model parameters, wherein the correction unit is further configured to determine the noise effect dataset by applying the model parameters determined to the physics model; and
- a second interface implemented by the processing facility, the second interface configured to output a correction result.

20. The correction system of claim 19, wherein correction of the x-ray image data comprises scattered radiation correction of the x-ray image data.

* * * * *